United States Patent
Ramanujam et al.

(10) Patent No.: US 10,266,463 B2
(45) Date of Patent: Apr. 23, 2019

(54) PROCESS FOR RECOVERING ISOPRENE FROM PYROLYSIS GASOLINE

(71) Applicant: GTC Technology US LLC, Houston, TX (US)

(72) Inventors: Venkata K. Ramanujam, Sugar Land, TX (US); Michael McCaulley, Sugar Land, TX (US); Joseph C. Gentry, Houston, TX (US)

(73) Assignee: GTC Technology US LLC, Houston, TX (US)

( * ) Notice: Subject to any disclaimer, the term of this patent is extended or adjusted under 35 U.S.C. 154(b) by 540 days.

(21) Appl. No.: 14/680,967

(22) Filed: Apr. 7, 2015

(65) Prior Publication Data
US 2015/0283478 A1   Oct. 8, 2015

Related U.S. Application Data

(60) Provisional application No. 61/976,386, filed on Apr. 7, 2014.

(51) Int. Cl.
| | |
|---|---|
| C07C 7/04 | (2006.01) |
| C07C 7/10 | (2006.01) |
| C07C 7/08 | (2006.01) |
| C10G 7/00 | (2006.01) |
| B01D 3/40 | (2006.01) |
| C07C 11/18 | (2006.01) |
| C07C 7/00 | (2006.01) |

(52) U.S. Cl.
CPC .......... *C07C 7/08* (2013.01); *B01D 3/40* (2013.01); *C07C 7/005* (2013.01); *C07C 7/10* (2013.01); *C07C 11/18* (2013.01)

(58) Field of Classification Search
None
See application file for complete search history.

(56) References Cited

U.S. PATENT DOCUMENTS

| | | | |
|---|---|---|---|
| 4,401,838 A * | 8/1983 | Balogh | C07C 7/14875 208/236 |
| 6,958,426 B2 | 10/2005 | Tian et al. | |
| 2010/0174126 A1* | 7/2010 | Loescher | C07C 2/08 585/314 |
| 2016/0122265 A1* | 5/2016 | Abdelghani | C07C 7/08 585/810 |

* cited by examiner

*Primary Examiner* — Neil N Turk
(74) *Attorney, Agent, or Firm* — Winstead PC

(57) ABSTRACT

Apparatuses, systems and methods for extracting isoprene using minimum capital investment, operating cost, and relatively corrosion free environment are disclosed herein. Embodiments of the invention are directed to producing pure isoprene and gasoline quality raffinate (free or sulfur and acetylenes) which are of value in manufacturing rubbers and other polymers.

5 Claims, 6 Drawing Sheets

PROCESS FOR RECOVERING ISOPRENE FROM PYROLYSIS GASOLINE

CROSS-REFERENCES TO RELATED APPLICATIONS

This Application claims the benefit under 35 U.S.C. § 119(e) of U.S. Provisional Patent Application No. 61/976,386 filed Apr. 7, 2014 which is incorporated herein by reference in its entirety as if fully set forth herein.

BACKGROUND OF THE INVENTION

In one aspect, this invention relates to the separation of selected compounds in a pyrolysis gasoline stream mainly Isoprene with minimum energy consumption. Isoprene is separated from hydrocarbons by extractive distillation. In another aspect, this invention relates to the use of a mixture of sulfolane (tetramethylene sulfone) alone or in combination with water and thiophene oxides as the solvent (also referred to as extractant or entrainer) in the aforementioned extractive distillation.

Extractive distillation is a well-known technique for separating mixtures of components having a relative volatility close to unity (i.e., having nearly equal volatility and having nearly the same boiling point). It is difficult to separate the components of such mixtures by conventional fractional distillation. In extractive distillation, a solvent is introduced into a distillation column above the entry point of the feed mixture which is to be separated. The presence of the solvent in the column alters the relative volatility of the compounds present in a direction to make the separation greater, and thus, to require either fewer stages to effect the same separation or to make possible a greater degree of separation with the same number of stages. The solvent affects the volatility of the higher boiling feed component(s) sufficiently to facilitate the separation of the various feed components, and it exits with the bottoms fraction, as has been described.

The separation of isoprene, from a close-boiling C5 hydrocarbon mixture (pyrolysis gasoline) by extractive distillation is known and has been described. However, there is a need for the development of more selective solvents than those presently known in the extractive distillation of pyrolysis gasoline components to reduce the net energy consumption and capital investment and corrosion and water treatment related issues that are common with existing solvents. In particular, it is desirable to develop improved extractive distillation processes for producing isoprene of high purity, both with more selective solvents and by other techniques and combination of both, since this compound is an important starting material for various chemicals, polymers and rubbers.

FIELD OF INVENTION

It is an object of this invention to provide a process to produce high purity Isoprene, from a pyrolysis gasoline stream containing close-boiling hydrocarbons by extractive distillation employing a selective solvent (also referred to as an extractant or entrainer). It is another object of this invention to provide a novel extractant mixture comprising a hydrocarbon solvent(s) and water. It is another object of this invention to improve the isoprene purification section for low energy consumption and with low capital investment in combination with extractive distillation for separating close boiling hydrocarbons that are extracted with isoprene by extractant compared to current processes.

Further in accordance with this invention, a process is provided for separating isoprene, from pyrolysis gasoline by extractive distillation from a pyrolysis gasoline feed containing a significant amount of isoprene, which employs a preferred solvent consisting essentially of sulfolane, in a mixture with thiophene oxides and water.

Still further in accordance with the invention, processes are provided consisting of multiple steps such as pretreatment of crude isoprene stream for sulfur removal and acetylene hydrogenation and post treatment of enriched isoprene stream using heat integrated pressure swing distillation to produce high quality isoprene from a pyrolysis gasoline feed stock.

Other objects and advantages will be apparent from the detailed description of the invention which follows, and the appended claims.

The claimed invention and the apparatuses and methods are intended to obtain polymer grade isoprene Such apparatuses and methods would allow more efficient operation and system design and operating conditions producing polymer grade isoprene with minimum energy consumption and minimum capital investment and durable less corrosive stable operation.

SUMMARY OF INVENTION

In accordance with a preferred embodiment of the invention, a process is provided for separating isoprene from at least one close-boiling hydrocarbon by extractive distillation of a feed containing isoprene and at least one close-boiling hydrocarbon, by employing a solvent consisting essentially of two or three components. The process produces an overhead product containing large percentage of close boiling hydrocarbon mixture and a insignificant volume percentage of isoprene than the feed; and a bottoms product containing a solvent and a larger volume percentage of isoprene and a smaller volume percentage of the close boiling yet extractable hydrocarbon than the feed. Enriched Isoprene and the smaller percentage close boiling hydrocarbons are separated from the solvent and recovered from the bottoms product. Enriched isoprene is separated purified to polymer grade isoprene quality by separating from the close boiling hydrocarbons using heat integrated pressure swing distillation system.

Preferably two components of the solvent is selected from the group consisting of propylene carbonate, sulfolane (tetramethylene sulfone), methyl carbitol, 1-methyl-2-pyrrolidinone, 2-pyrrolidinone, and mixtures thereof, and the third component is water. The preferred component of the solvent from the group of organic components listed is sulfolane.

In another preferred embodiment, the close boiling hydrocarbons are Pentane, Cis-Pentene, Trans Pentene, 1-pentene, 2 methyl 1 Butene, 2 methyl 2 butene, Cis and Trans 1,3 Pentadiene, Cyclopentadienes and Pentynes as a minimum.

The preferred range for the weight ratio of solvent to feed is in the range of about 0.5:1 to about 50:1, more preferably 7:1 and 10:1. It is also preferred that the feed boil at a temperature in the range of about 30 to 60° C.

The boiling point of isoprene and the boiling point of said at least one hydrocarbon may preferably differ by about 0.1-10 degree.

In further accordance with the invention, a process is provided for separating isoprene from at least one close-boiling hydrocarbon by extractive distilling the mixture thereof in the presence of a ten-part extractive solvent the first two parts of which is selected from the group consisting of propylene carbonate, sulfolane (tetramethylene sulfone), methyl carbitol, 1-methyl-2-pyrrolidinone, 2-pyrrolidinone, and mixtures thereof, and the third part of which is water, to obtain a solvent fraction relatively rich in isoprene, and stripping isoprene from said solvent fraction. It is particularly preferred that the at least one close-boiling hydrocarbon is one among the aforementioned components. It is also preferred that the weight proportion of the second and third part of said extractive solvent to the first part thereof is from about 0% to about 50%, more preferably between 2 to 15%.

In accordance with another aspect of the invention, a process is provided for producing isoprene from a feedstock comprising isoprene and at least one close-boiling hydrocarbon by feeding said feedstock into a distillation zone, feeding ten-parts extractive solvent into said distillation zone, said solvent consisting essentially of a first two parts selected from the group consisting of propylene carbonate, sulfolane (tetramethylene sulfone), methyl carbitol, 1-methyl-2-pyrrolidinone, 2-pyrrolidinone, and mixtures thereof and the third part consisting of water, distilling said feedstock in said distillation zone in the presence of said extractive solvent to produce a solvent fraction relatively rich in isoprene compared to the solvent fed to said distillation zone, and an overhead fraction comprising said at least one close-boiling hydrocarbon and being relatively lean in isoprene compared to said feedstock, withdrawing said solvent fraction from said distillation zone and withdrawing said overhead fraction from said distillation zone.

In a preferred form of said process, the ten parts of said three-part extractive solvent are fed to said distillation zone separately. The preferred feedstock is pyrolysis gasoline or crude isoprene stream.

A further preferred embodiment of the invention is one in which said feedstock is formed by fractionating a pyrolysis gasoline to produce a C5 stream comprised mainly of hydrocarbons containing 5 carbons, said C5 stream constituting the feedstock fed to said distillation zone. Furthermore, said C5 stream may be hydrogenated before being fed to said distillation zone to hydrogenate any acetylenic compounds therein, and the hydrogenation of said C5 stream is preferably effected under conditions avoiding conversion of substantial amounts of isoprene and other hydrocarbons containing one or two double bonds.

A further preferred embodiment of the invention said C5 stream may be treated for removing sulfur compounds before being fed to hydrogenation and said distillation zone.

It is further preferred that the invention be practiced in such a way that at least a portion of said overhead fraction is hydrogenated to produce a mixture containing pentanes or saturated C5 compounds.

In addition, the above-mentioned solvent fraction is desirably fed to a stripping zone in which isoprene, a portion of said close boiling hydrocarbon, and water are separated into a stripper overhead stream from solvent, which then constitutes a lean solvent bottom stream, and which is recycled to said distillation zone as the first part of said three-part extractive solvent. Further, the stripper overhead stream is preferably fed to a isoprene purification zone consisting of heat integrated pressure swing distillation columns in which hydrocarbon components, including cyclopentadiene, which are heavier than isoprene and water, are separated into a heavies bottom stream, purified isoprene is separated into a isoprene purifier overhead stream. The isoprene purifier bottom stream is then preferably recycled to upstream pyrolisis gasoline separation section where C5 fraction is separated.

Further more the isoprene purification zone consists of low pressure distillation column operating under vacuum conditions between full vacuum to atmospheric pressure and a high pressure rectification column operating at a pressure 1 to 5 times greater, preferably between 1.5 to 3 times greater than the low pressure stripping column.

In addition the low pressure overhead is compressed and introduced to the high pressure rectification column as a stripping medium and the high pressure rectification column bottoms are flashed and introduced as reflux to low pressure stripping column.

In addition the overhead condensing system of the high pressure rectification column and the reboiling system of low pressure stripping column are heat integrated by a freeze protected liquid, cooling water, hydrocarbon stream or direct coupling or in combination.

In addition a pump around heater is provided from the low pressure stripping system to satisfy the overhead condensing duty of solvent recovery column. The pump around heater can be either pump down or pump up system and is taken from an appropriate location to satisfy the temperature gradient as required by solvent recovery column overhead.

Furthermore, in the above-described processes, water is preferably separated from the overhead streams issuing from said extractive distillation zone, said stripping zone, and said isoprene purification zone, and is returned to said distillation zone as at least a portion of said third part of said three-part extractive solvent.

Preferably, the weight ratio of said three-part extractive solvent to said feedstock is between about 1:1 and about 20:1, the feedstock boils at a temperature in the range of from about 30-60° C., and the boiling point of said isoprene and said at least one close-boiling hydrocarbon differ by from about 0.1° C. to about 10° C.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION OF EXEMPLARY EMBODIMENTS

Figure 1:
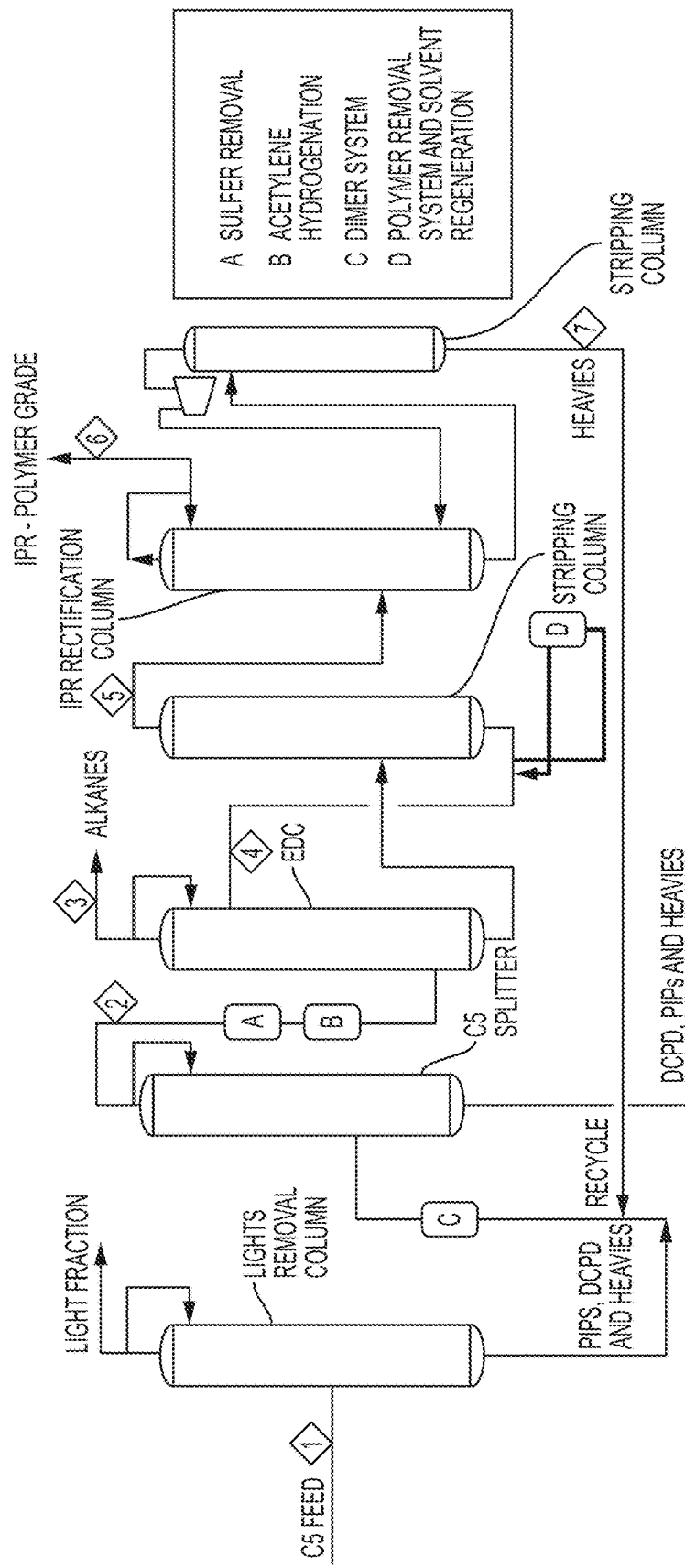
FIG. 1 shows an illustrative isoprene extraction process.

In an extractive distillation process, an agent (called "solvent" or "extractant" or "entrainer") is added to a feed mixture of components to be separated, so that the relative volatilities of the components of the mixture are changed such that a sufficient difference in volatility of the components results, and effective separation by distillation becomes possible. The added solvent is usually chosen so as to exhibit high "selectivity" regarding the components to be separated. Selectivity is a term related to the change in volatilities of components in the mixture caused by the presence of the solvent. The larger the difference in relative volatility of the components in the mixture, the easier the separation of the components by fractional distillation becomes. Therefore, a solvent of high selectivity causes great differences between the relative volatilities of the components in a mixture, and will allow for the separation of components in a mixture with fewer distillation stages, a lower amount of reflux, and higher product purity. The term "close-boiling" as used herein, means that the feed components have nearly the same boiling point at the conditions of the distillation.

Any hydrocarbon feed which contains isoprene and at least one hydrocarbon, which is close-boiling with it, can be used in the process of this invention.

Non-limiting examples of suitable feed components are Acetylene and Butadiene both of which are common in pyrolysis gasolines. Such components may also be found in other hydrocarbon feedstocks such as coal tar liquids, catalytically reformed naphtha, on purpose isoprene stream.

Any suitable weight ratio of the solvent to the hydrocarbon-containing feed mixture can be employed. Preferably, the solvent-to-feed weight ratio is in the range of about 0.5:1 to about 50:1, and more preferably between about 7:1 and about 10:1.

Any suitable total column height, packed column height, column diameter and number of trays in the extractive distillation column can be employed. The exact dimensions and column designs depend on the scale of the operation, the exact feed composition, the exact solvent composition, the desired recovery and the degree of purity of the sought-after substituted unsaturated aromatic product, and like considerations.

The following examples are presented to further illustrate the invention and are not to be considered as unduly limiting the scope of this invention.

In the following description, certain details are set forth such as specific quantities, sizes, etc. so as to provide a thorough understanding of the present embodiments disclosed herein. However, it will be obvious to those skilled in the art that the present disclosure may be practiced without such specific details. In many cases, details concerning such considerations and the like have been omitted inasmuch as such details are not necessary to obtain a complete understanding of the present disclosure and are within the ability of persons of ordinary skill in the relevant art.

Referring to the drawings in general, it will be understood that the illustrations are for the purpose of describing a particular embodiment of the disclosure and are not intended to be limiting thereto. Drawings are not necessarily to scale.

While most of the terms used herein will be recognizable to those of skill in the art, it should be understood, however, that when not explicitly defined, terms should be interpreted as adopting a meaning presently accepted by those of skill in the art.

"Raffinate," as used herein, refers to, for example, light hydrocarbons that are close boiling to isoprene but are not extracted;

In the thermal cracking in the presence of steam of liquid fractions of petroleum, such as LPG, Naphtha, Diesel and heavies for production of ethylene and or propylene, a hydrocarbon liquid fraction called Pyrolysis Gasoline, is produced. This Pyrolysis Gasoline consists of hydrocarbon components ranging from 4 carbon atoms to more than 10 carbon atoms. Among these, of importance to the field of innovation are isoprene, cyclopentadiene (CPD), cis and/or trans 1,3 pentadienes (Pips), Isoprene, 2-methylbutene-1,2-methyl-butene-2, and similar hydrocarbon molecules containing 5 carbons. Isoprene is used predominantly to make rubber and in certain block copolymers.

In various embodiments, apparatuses for obtaining streams consisting of single component, specifically isoprene are disclosed. The apparatuses comprise: Sulfur removal system consisting of chemicals, mixers, and liquid extraction column, Hydrogenation reactor, Distillation columns, heat exchangers for condensers and reboilers, Distillation columns connected by compressor. The apparatuses are operated continuously.

An embodiment of the invention is directed to a process for the production of isoprene using a system that employs a specific arrangement of apparatuses and operating conditions to enhance the separation of isoprene, while at the same time consuming less energy, less capital and with minimum operational instability.

The crude isoprene fraction obtained by pre fractionating the pyrolosis gasoline is subsequently subjected to sulfur treatment process to remove the sulfur containing compounds, particularly carbon disulfide, a selective hydrogenation step to saturate the acetylene compounds, preferably with minimum loss of isoprene, single stage extractive distillation column/solvent recovery column (EDC/SRC) system, heat integrated differential pressure distillation system for purifying the enriched hydrocarbon from the close boiling extracted hydrocarbons.

FIG. 1 shows a process for recovering isoprene from a C5 feedstock. In this process, the feedstock (1) is introduced to a deisopentanizer. The lights fraction containing C4s and isopentane is removed in an overhead fraction of the deisopentanizer. Cyclopentadienes are removed in a bottoms fraction of the deisopentanizer. The cyclopentadienes are subjected to dimerization in a dimerization system (C), following which the product of dimerization is introduced to a C5 splitter. The crude isoprene stream product from the overhead stream of the C5 splitter (2) is introduced to an extractive distillation step after removing sulfur (A) and hydrogenating-saturating C5 acetylenes (B). The bottoms fraction of the extractive distillation column, which is rich in isoprene, is transferred to a solvent recovery column. The overhead stream (3) of extractive distillation which is raffinate containing majority alkanes, is sent back to the extractive distillation column for either re-cracking or for blending to gasoline pool. The overhead stream from the solvent recovery column (5) is transferred to an isoprene rectification column. The lean solvent (4) from the bottoms of the solvent recovery column is recycled back to extractive distillation as an extraction agent (D). Pure isoprene (6) is withdrawn from the overhead stream of the isoprene rectification column. The bottoms fraction of the isoprene rectification column is transferred to a stripping column. The overhead fraction of the stripping column is transferred to the isoprene rectification column. The bottoms fraction of the stripping column is transferred to the dimerization system (C).

Figure 2:
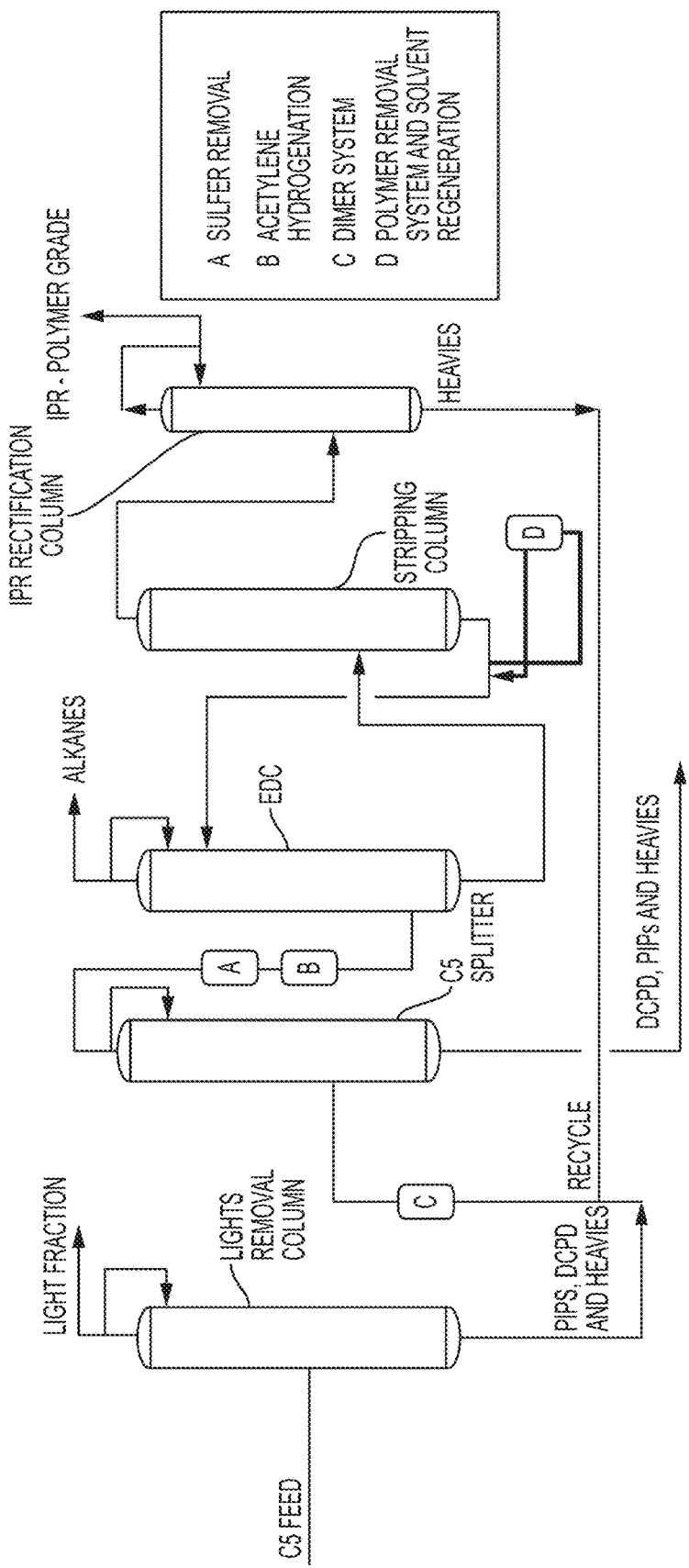
FIG. 2 shows an illustrative alternate isoprene extraction process.

In FIG. 2, an alternate embodiment of the invention is depicted wherein the stripping column that follows the isoprene rectification column is not included.

Figure 3:
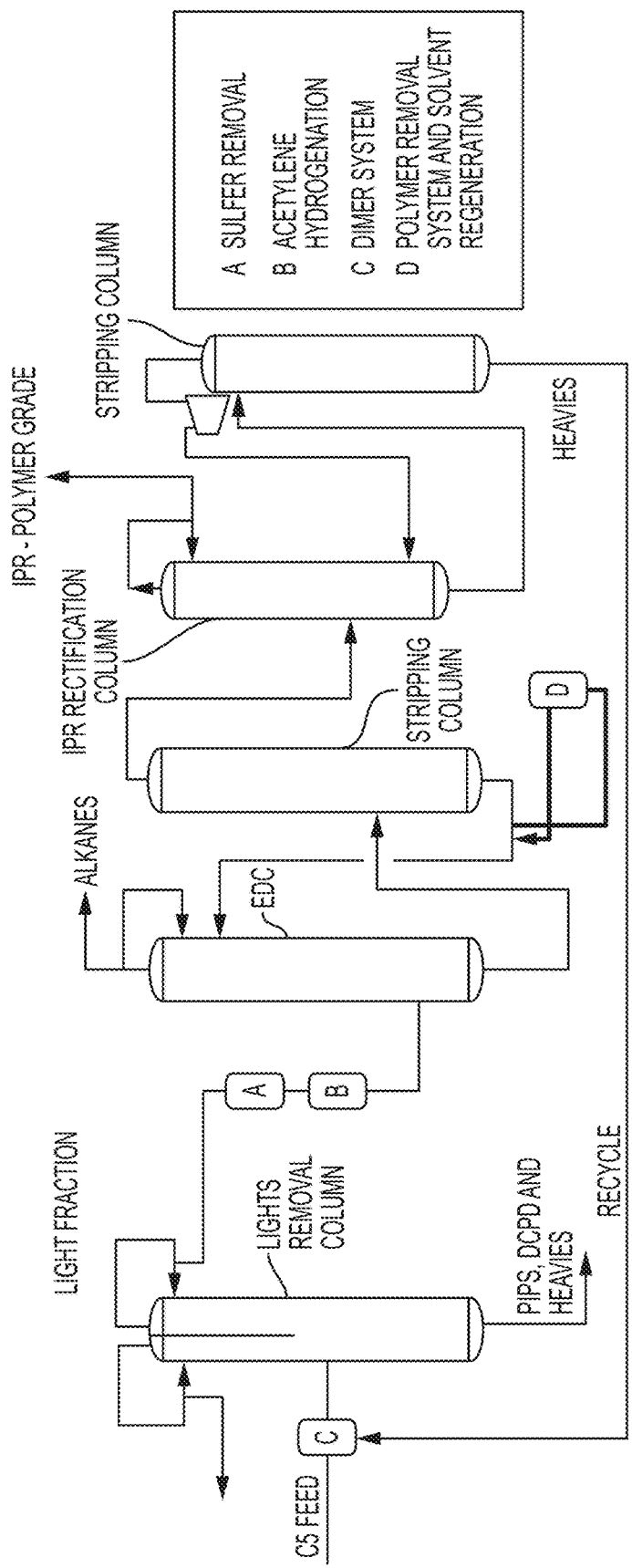
FIG. 3 shows an illustrative alternate isoprene extraction process with a Top Divided wall Column.

In FIG. 3, an alternate isoprene extraction process with a Top Divided wall Column is shown. The top-divided column performs the function of the deisopentanizer and the C5 splitter.

Figure 4:
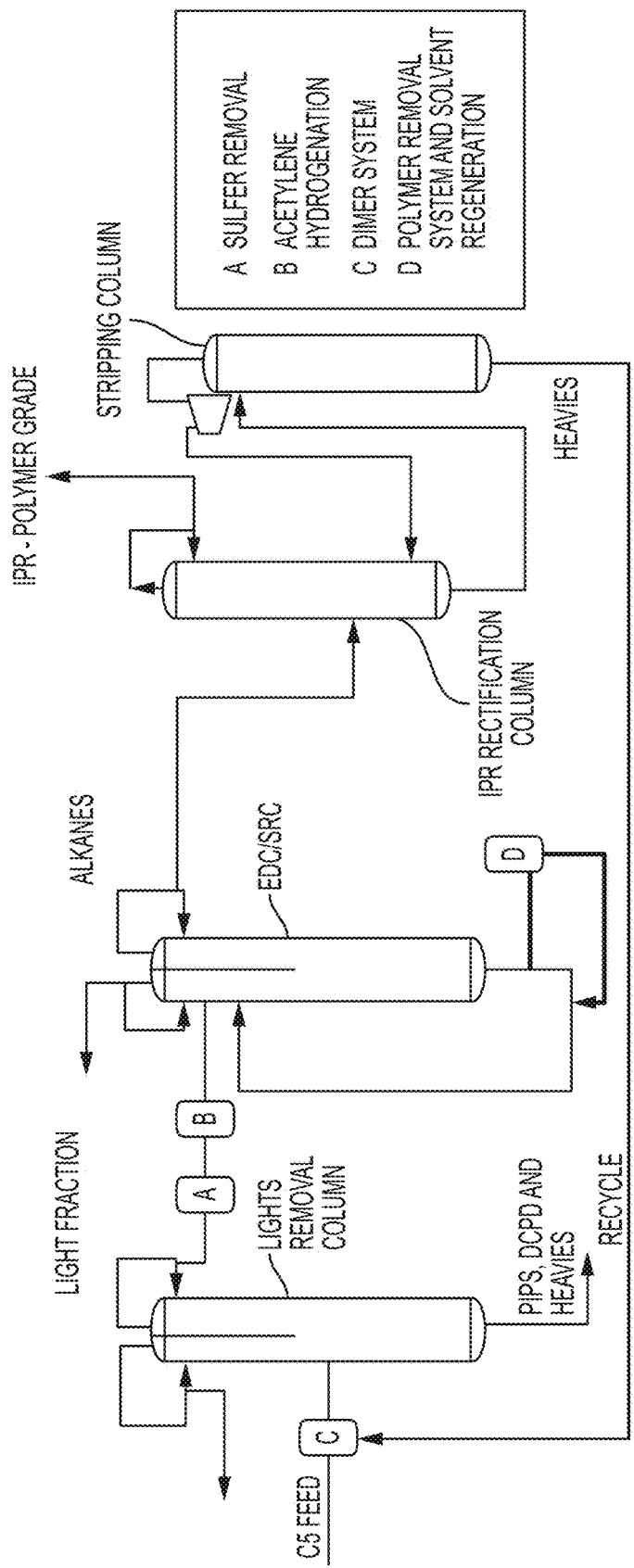
FIG. 4 shows an illustrative alternate isoprene extraction process with 2 Top Divided wall Columns for lights removal and extraction/solvent recovery column.

In FIG. 4, an alternate isoprene extraction process with a 2 Top Divided wall Columns is shown. The first top divided wall column performs the function of the deisopentanizer and the C5 splitter. The second top divided column performs the function of the solvent recovery column and the extractive distillation column.

Figure 5:
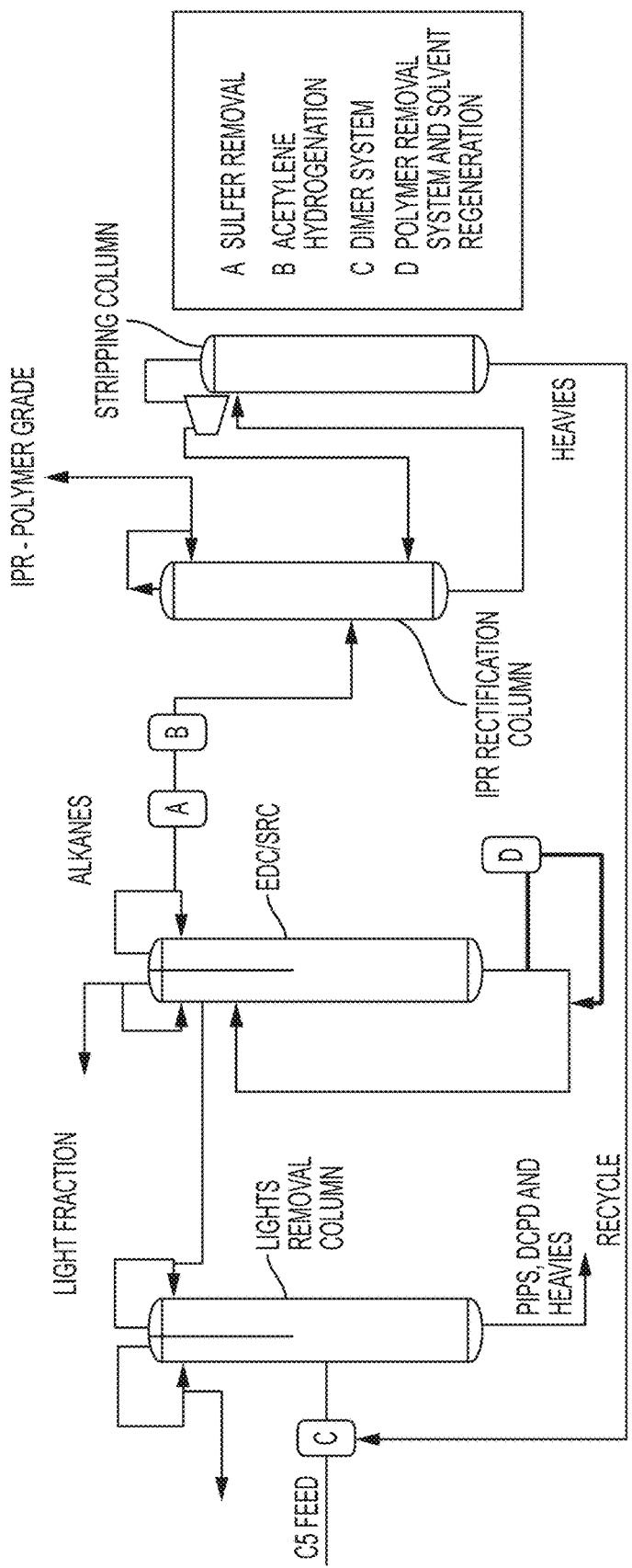
FIG. 5 shows an illustrative alternate isoprene extraction process with 2 Top Divided wall Columns for lights removal and extraction/solvent recovery column.

In FIG. 5, an alternate isoprene extraction process with a 2 Top Divided wall Columns is shown. The first top divided wall column performs the function of the deisopentanizer and the C5 splitter. The second top divided column performs the function of the solvent recovery column and the extractive distillation column. The sulfur removal and acetylene hydrogenation steps in this embodiment take place after the second top divided column.

Figure 6:
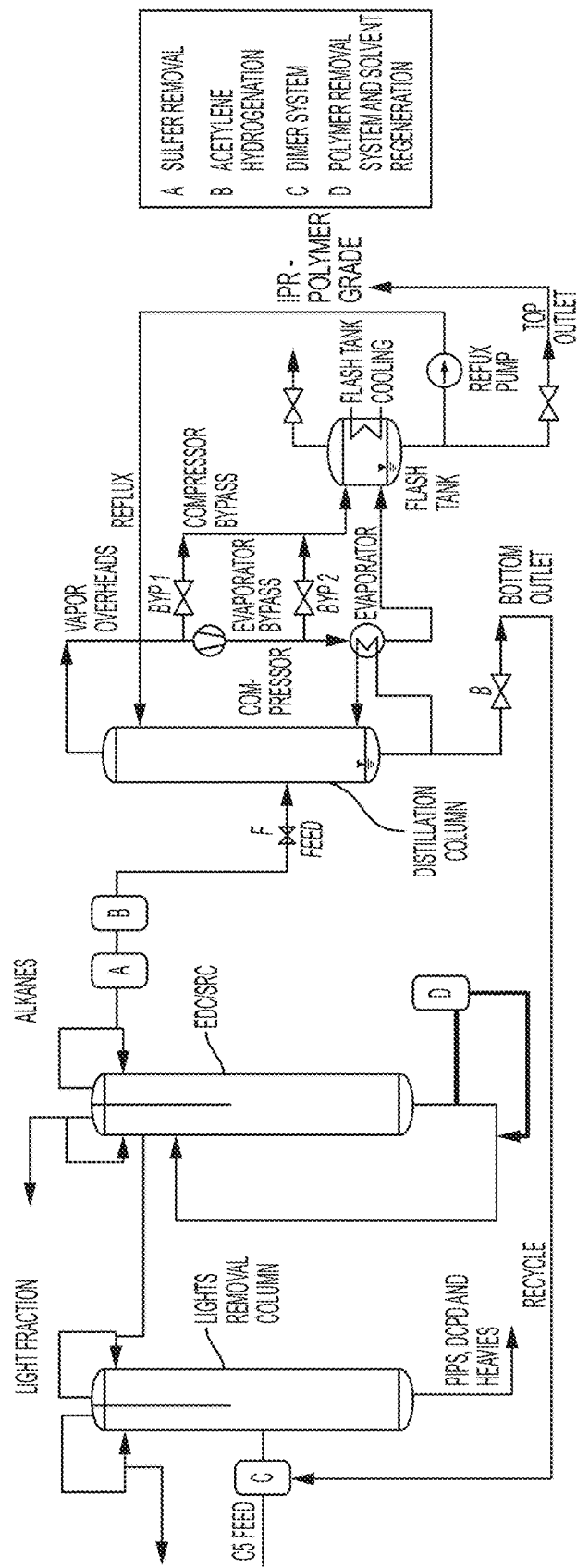
FIG. 6 shows an illustrative alternate isoprene extraction process using vapor recompression cycle.

In FIG. 6, an alternate isoprene extraction process using vapor recompression cycle is shown. The vapor recompression step is added downstream of the distillation or stripping columns. The vapor recompression step can be added to any of the processes shown in FIGS. 1-5.

Example 1

This example demonstrates the scheme and the solvent, preferably two components selected from the group consisting of propylene carbonate, sulfolane (tetramethylene sulfone), methyl carbitol, 1-methyl-2-pyrrolidinone, 2-pyrrolidinone, and mixtures thereof, and the third component is water.

The scheme uses following C5 Cut of the pygas obtained from the depentanizer overhead.

| Component | Weight % |
| --- | --- |
| C4s & lower | 3.00 |
| 3-methyl butene-1 | 0.80 |
| 1-4-Pentadiene | 1.80 |
| 2-Butyne | 0.66 |
| iso-Pentane | 12.16 |
| 1-Pentene | 2.63 |
| 2-methylbutene-1 | 4.63 |
| Isopryne (2-methyl-1-butene-3-yne) | 0.20 |
| Isoprene | 17.50 |
| n-Pentane | 22.00 |
| trans-2-Pentene | 2.20 |
| cis-2-Pentene | 1.30 |
| 2-methylbutene-2 | 1.90 |
| 1-Pentyne | 0.41 |
| 1,3-Cyclopentadiene | 10.00 |
| 1-Pentene-4-yne | 0.08 |
| Cyclopentene | 3.10 |
| Cyclopentane | 1.60 |
| 2-Pentyne | 0.05 |
| Other C5s | 0.67 |
| CS2 | 0.08 |
| Total Piperylenes | 12.00 |

As shown in FIG. 1, the feed stream "1" as defined above, containing above composition is introduced to Deisopentanizer to remove the lights such as C4's, Isopentane etc. The heavies from the bottom are subject to Dimerization to dimerize the Cyclopentadienes to Dicyclopentadienes. The dimerizer product is introduced to C5 splitter to separate the heavies from isoprene and co-boiling components as crude isoprene stream "2". The Crude isoprene stream is introduced to Extractive distillation step after removing sulfur and saturating C5 acetylenes. The overhead stream "3" of extractive distillation is raffinate containing majority alkanes is sent back for either re-cracking or for blending to gasoline pool. Isoprene rich solvent from the bottom of extractive distillation is introduced to solvent recovery column for stripping isoprene from solvent. The lean solvent "4" from the bottom the solvent recovery column is recycled back to extractive distillation as an extraction agent. The isoprene concentrate stream "5" from the over head is introduced to IPR rectification column. Pure isoprene stream "6" is withdrawn as overhead stream. Bottoms from the IPR rectification column are introduced at the top of stripping column. Overheads from the stripping column are compressed and recycled back to IPR rectification column. Heavy impurities from the isoprene concentrate are withdrawn as bottom product "7" from the stripping column and are recycled to upstream dimerization section.

Heat and mass balance corresponding to referred stream numbers in para. 50 are provided below in Table 1.

TABLE 1

| | Stream Number | | | | | |
| --- | --- | --- | --- | --- | --- | --- |
| | 2 | 3 | 4 | 5 | 6 | 7 |
| Phase | Liquid | Liquid | Liquid | Liquid | Liquid | Liquid |
| Total Mass Rate | 8875.2 | 5636.0 | 87251.8 | 4082.8 | 2916.2 | 160.7 |
| H2O | 0.00 | 1.89 | 2595.23 | 1.32 | 0.99 | 0.00 |
| Sulfolan | 0.00 | 0.00 | 84656.53 | 0.00 | 0.00 | 0.00 |
| C4 and other C5s | 1766.35 | 1755.12 | 0.00 | 3.66 | 3.16 | 1.77 |
| Isoprene | 2925.49 | 23.33 | 0.00 | 3868.56 | 2908.52 | 0.64 |
| Pentane | 3964.27 | 3841.58 | 0.00 | 0.00 | 2.65 | 2.27 |
| Neopentane | 0.00 | 0.00 | 0.00 | 0.00 | 0.00 | 0.00 |
| 2-methyl butene-1 | 3.23 | 0.00 | 0.00 | 4.30 | 0.00 | 3.05 |
| 2-methyl butene-2 | 57.00 | 13.99 | 0.00 | 56.74 | 0.00 | 42.42 |
| 3-methyl butene-1 | 0.91 | 0.12 | 0.00 | 1.05 | 0.79 | 0.00 |
| 1-Pentyne | 12.06 | 0.00 | 0.00 | 0.00 | 0.00 | 0.00 |
| 2-Pentyne | 0.00 | 0.00 | 0.00 | 0.00 | 0.00 | 0.00 |
| 1-penten-3-yne | 0.00 | 0.00 | 0.00 | 0.00 | 0.00 | 0.00 |
| 2-methyl-1-buten-3-yne | 35.42 | 0.00 | 0.00 | 0.00 | 0.00 | 0.00 |
| 1-Penten-4-yne | 0.09 | 0.00 | 0.00 | 0.00 | 0.00 | 0.00 |
| Cis 1,3, pentadiene | 1.20 | 0.00 | 0.00 | 1.59 | 0.00 | 1.20 |
| Trans 1,3, pentadiene | 13.54 | 0.00 | 0.00 | 18.05 | 0.00 | 13.55 |
| Cis 1,3 diene | 83.32 | 0.00 | 0.00 | 111.09 | 0.00 | 83.48 |
| Other C5s | 12.32 | 0.01 | 0.01 | 16.41 | 0.09 | 12.33 |

What is claimed is:

1. A process for producing isoprene from a feedstock, the process comprising the steps of:
   feeding a C5 feedstock comprising isoprene and at least one sulfur compound to a top divided wall column;
   removing from the top divided wall column a first overhead stream comprising C4 and isopentane and a second overhead stream comprising C5 and isoprene;
   feeding the second overhead stream comprising C5 and isoprene into an extractive distillation column;
   removing the at least one sulfur compound from the second overhead stream comprising C5 and isoprene before feeding the second overhead stream comprising C5 and isoprene to the extractive distillation column;
   feeding an extractive solvent into the extractive distillation column, the extractive solvent comprising at least two of the following: propylene carbonate, sulfolane (tetramethylene sulfone), methyl carbitol, 1-methyl-2-pyrrolidinone, 2-pyrrolidinone, and mixtures thereof;

distilling, in the extractive distillation column, the second overhead stream comprising C5 and isoprene in the presence of the extractive solvent;

producing, via the extractive distillation column, a bottoms fraction comprising isoprene and an overhead fraction comprising raffinate with alkanes;

feeding the bottoms fraction comprising isoprene to a solvent recovery column; recovering, via the solvent recovery column, solvent from the bottoms fraction comprising isoprene and feeding the recovered solvent to the extractive distillation column;

producing, via the solvent recovery column, an overhead stream comprising isoprene and feeding the overhead stream comprising isoprene to an isoprene rectification column; and wherein the extractive solvent further comprises at least one close-boiling hydrocarbon selected from the group consisting of pentane, cis-pentene, trans pentene, 1-pentene, 2 methyl 1 butene, 2 methyl 2 butene, cis 1,3 pentadiene, trans 1,3 pentadiene, cyclopentadienes, and pentynes.

2. The process of claim 1, further comprising removing hydrogenating-saturating C5 acetylenes from the second overhead stream comprising C5 and isoprene before feeding the second overhead stream comprising C5 and isoprene to the extractive distillation column.

3. The process of claim 1, wherein the extractive solvent further comprises water.

4. The process of claim 1, wherein the second overhead stream comprising C5 and isoprene is hydrogenated to produce a mixture comprising at least one of pentanes and saturated C5 compounds.

5. The process of claim 1, wherein a weight ratio of the extractive solvent to the C5 feedstock comprising isoprene and at least one sulfur compound is about 7:1 to about 10:1.

* * * * *